United States Patent [19]
Willis

[11] Patent Number: 5,147,395
[45] Date of Patent: Sep. 15, 1992

[54] SMALL INCISION ENDOCAPSULATOR IOL

[75] Inventor: Timothy R. Willis, Lake Forest, Calif.

[73] Assignee: Allergan Inc., Irvine, Calif.

[21] Appl. No.: 730,683

[22] Filed: Jul. 16, 1991

[51] Int. Cl.⁵ .............................................. A61F 2/16
[52] U.S. Cl. ........................................................ 623/6
[58] Field of Search ............................................ 623/6

[56] References Cited
U.S. PATENT DOCUMENTS

| | | | |
|---|---|---|---|
| 4,424,597 | 1/1984 | Schlegel | 623/6 |
| 4,468,820 | 9/1984 | Uhler et al. | 623/6 |
| 4,573,998 | 3/1986 | Mazzocco | 623/6 |
| 4,666,445 | 5/1987 | Tillay | 623/6 |
| 4,693,715 | 9/1987 | Abel, Jr. | 623/5 |
| 4,790,846 | 12/1988 | Christ et al. | 623/6 |
| 4,842,599 | 6/1989 | Bronstein | 623/5 |

Primary Examiner—Randy C. Shay
Attorney, Agent, or Firm—Gordon L. Peterson

[57] ABSTRACT

An intraocular lens comprising a deformable optic and at least one fixation member for use in fixing the optic in the eye. The fixation member includes a deformable element integral with the optic and at least one resilient stiffening element within in the optic and attached to the optic by the deformable element. The stiffening element stiffens the deformable element.

14 Claims, 5 Drawing Sheets

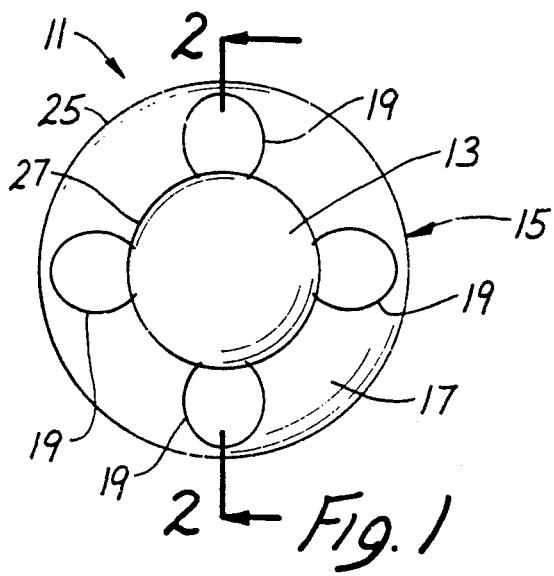
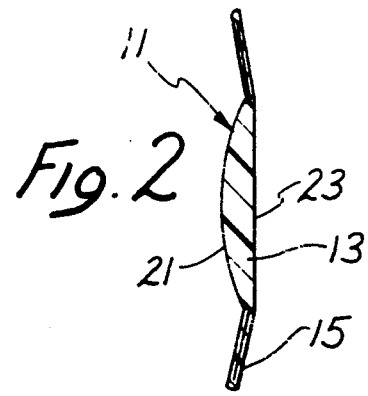
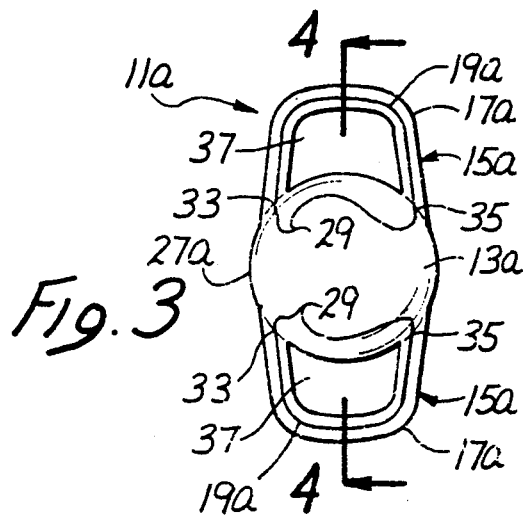
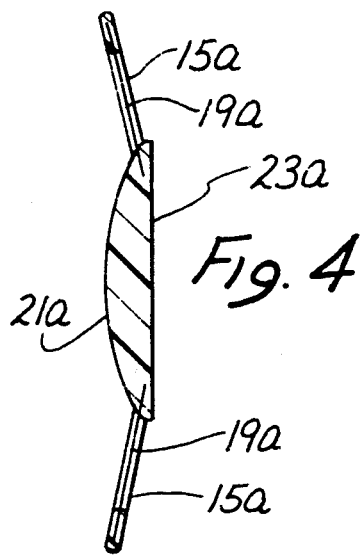
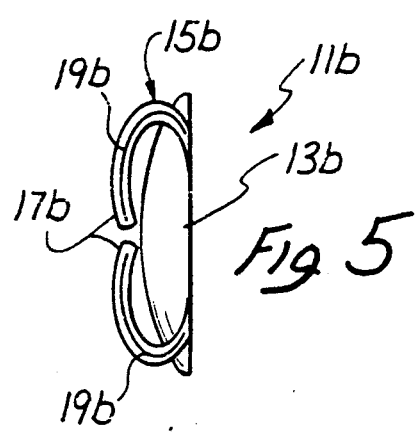

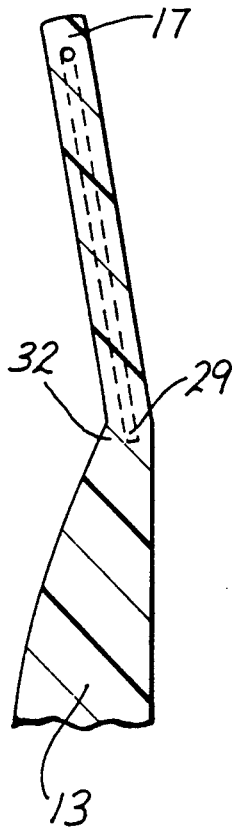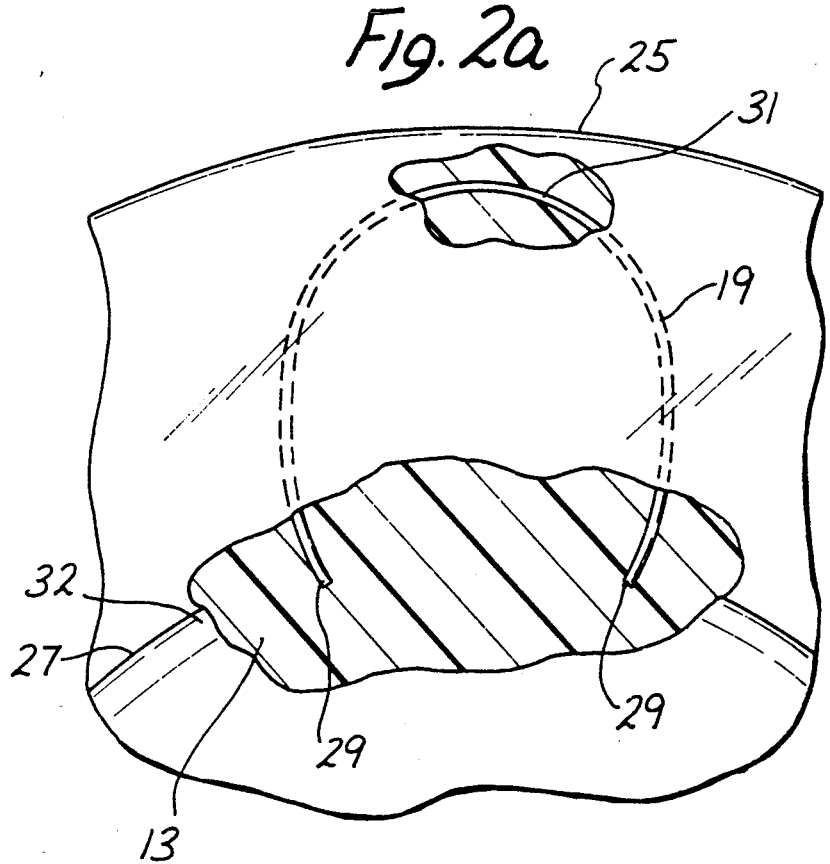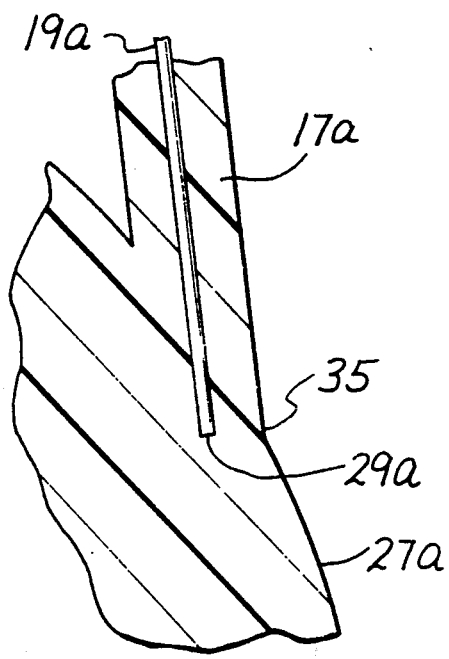

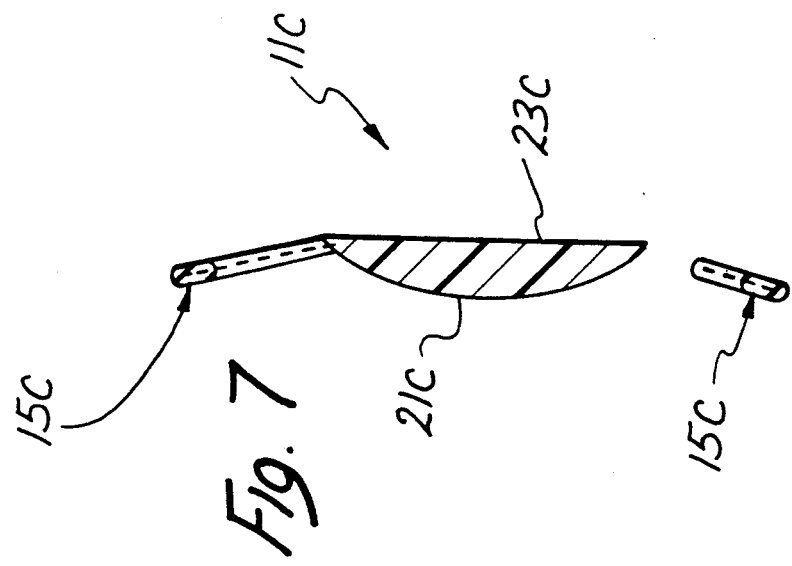
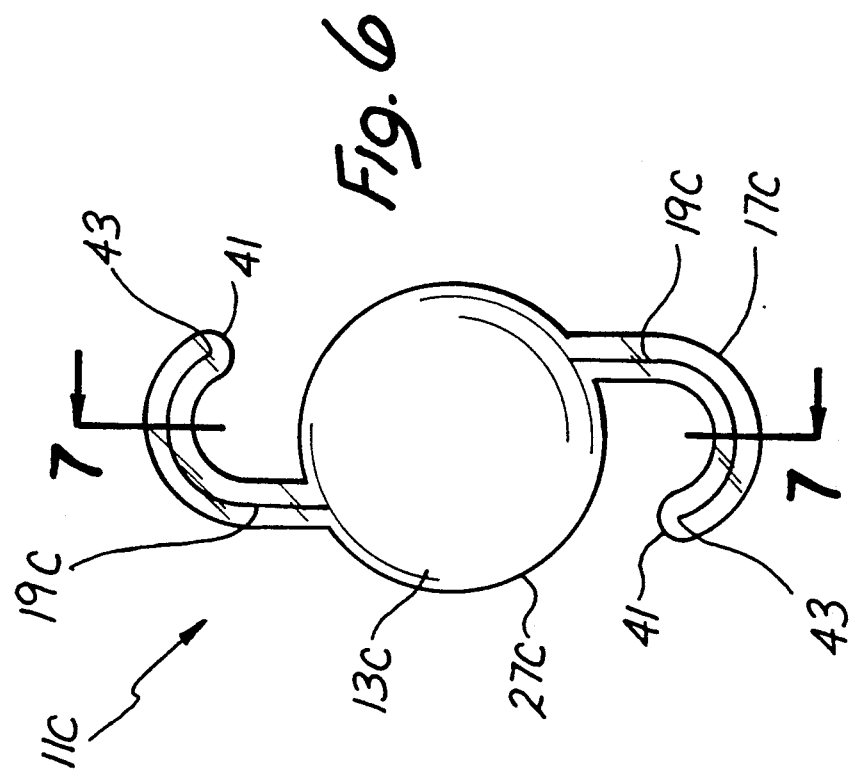

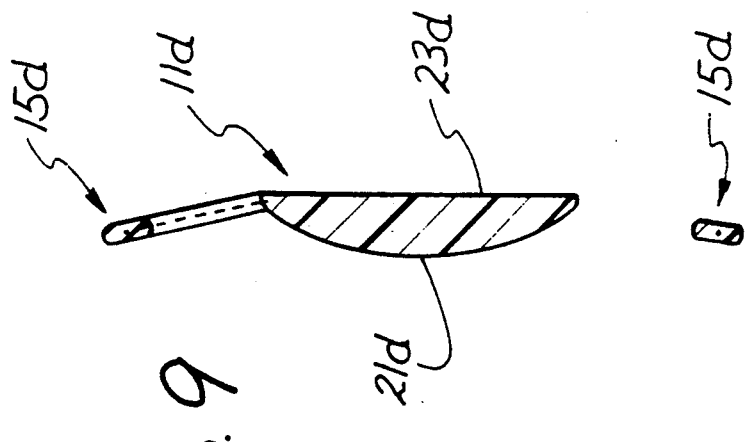
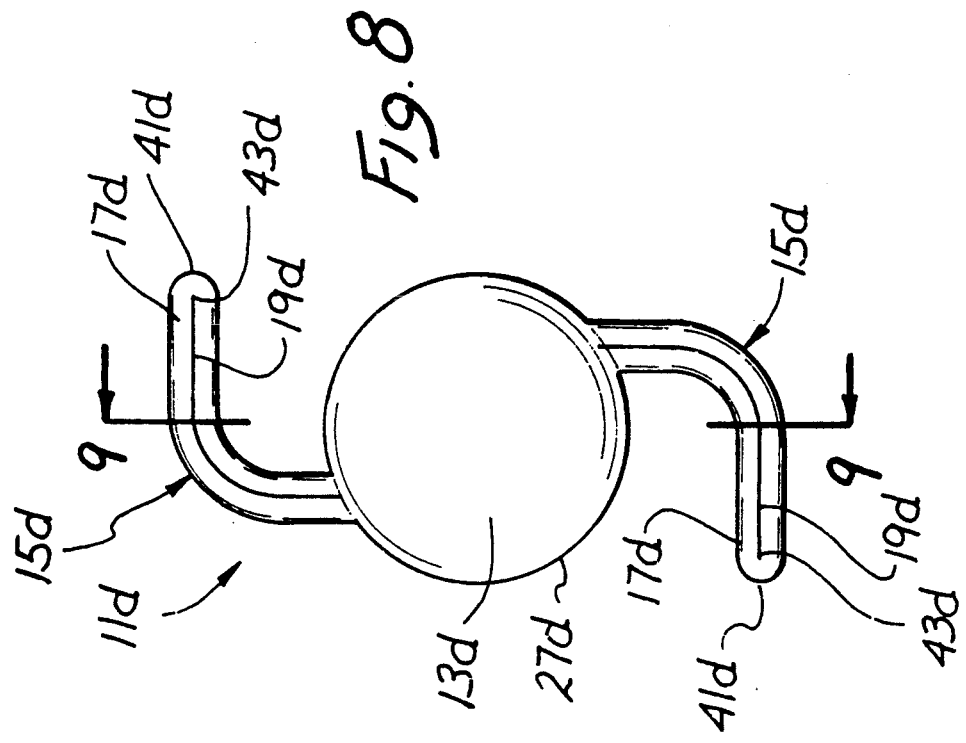

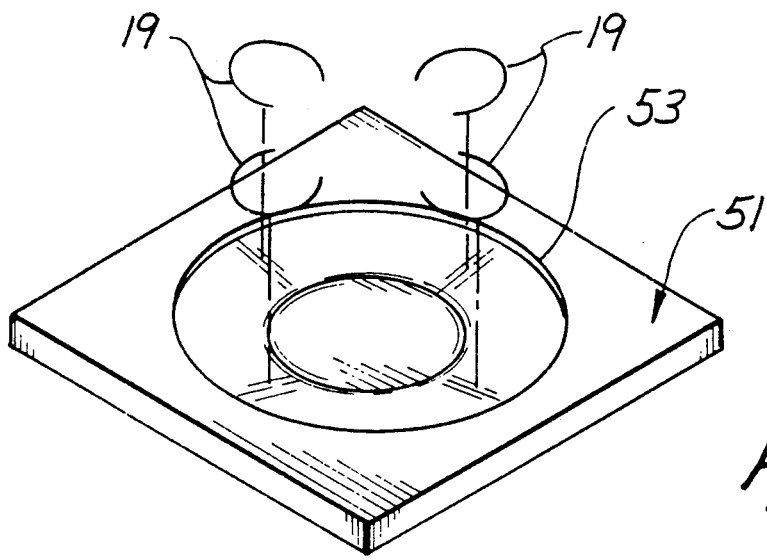
Fig. 10
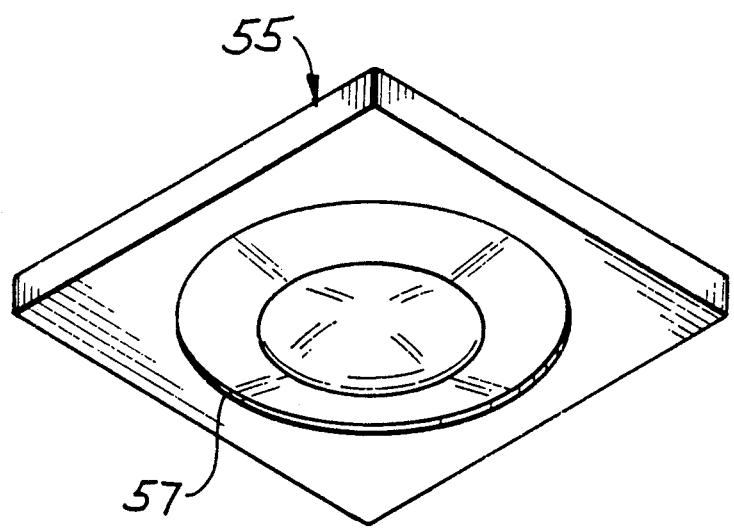
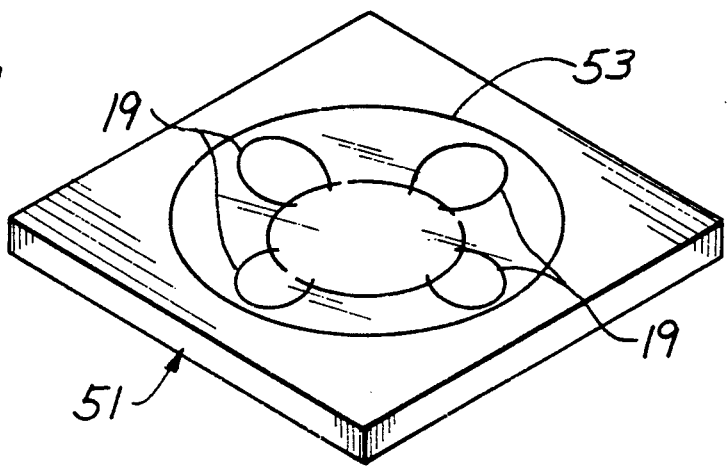
Fig. 11

SMALL INCISION ENDOCAPSULATOR IOL

FIELD OF THE INVENTION

This invention relates to an intraocular lens, and more particularly to an intraocular lens having a deformable optic which can be rolled or flexed for insertion through a relatively small incision into the eye.

BACKGROUND OF THE INVENTION

Whenever cataracts or other conditions require, the natural lens of the human eye can be removed and replaced with an intraocular lens (IOL). An intraocular lens comprises an optic or lens and one or more fixation members which are ordinarily formed of resilient filaments for fixing the optic in the proper position within the eye so that it can direct light toward the retina.

In one common form of intraocular lens, the optic is constructed of a rigid, non-deformable material such as polymethylmethacrylate (PMMA). In a second type of intraocular lens, the optic is constructed of a deformable material, such as silicone or hydrogel. A deformable optic can be rolled or folded for insertion through an ocular incision, which is smaller than the undeformed diameter of the optic. An important advantage of an intraocular lens having a deformable optic is that, when it is rolled or folded, it can be inserted through a smaller ocular incision than can a rigid IOL. This small incision reduces the trauma to the patient, heals faster than a larger incision needed for most rigid IOLs and provides other advantages.

One problem with an intraocular lens having a deformable optic is in the attachment of the fixation member or members to the optic. One way to accomplish this is to utilize separate fixation members and attach them to the optic. These separate fixation members, which are commonly constructed of PMMA or polypropylene, are typically fine hair-like strands. It is somewhat difficult to attach these fine hair-like strands to a deformable optic in a way that will assure that the strands will not pull out from the deformable optic. One way to address this problem is to shape the inner end portions of the strands so that it is difficult to pull them out of the optic. Examples of this are shown in Knight et al U.S. Pat. No. 4,834,751 and Christ et al U.S. Pat. No. 4,790,846.

Another approach is to employ fixation members which are constructed integrally with the optic (i.e. of the same material as the optic so as to form a one piece IOL). However, because of the soft, deformable nature of the foldable optic material, the integral fixation members would need to be large and relatively thick in order that they would have sufficient size to adequately retain and position the optic within the eye. However, thickening of the integral fixation members would give the rolled or folded intraocular lens a larger cross-sectional area than would exist without such thickening of the fixation members, and this, in turn, would require a larger incision than would otherwise be required for the optic alone.

SUMMARY OF THE INVENTION

This invention provides an intraocular lens which can be rolled or folded into a small cross-sectional area and which does not require any special shaping or processing of the inner end portions of the fixation members. With this invention, the intraocular lens includes at least one fixation member which includes a deformable element joined to the optic and a resilient stiffening element at least partly disposed within the deformable element.

The stiffening element and the deformable element coact in a novel way to provide significant advantages. For example, the stiffening element stiffens the deformable element. Consequently, the deformable element, which is formed integral with the optic, can be thinner than if the stiffening element were not employed. In addition, the deformable element is preferably used to attach, or assist in attaching, the stiffening element to the optic. Consequently, no special shaping or processing of the stiffening element is needed to accomplish the desired attachment. Also, by encasing the stiffening element in the deformable element, it may be possible to employ certain advantageous materials for the stiffening element that might not be safely usable in the eye without such encasing.

In order that the deformable element can attach the stiffening element to the optic, a sufficient portion of the stiffening element should be within the optic to achieve this result. At least a major region of the stiffening element is preferably received within the deformable element, and optimally, all or substantially all of the stiffening element is received within the deformable element.

The stiffening element can be of various different configurations. For example, the stiffening element may be an elongated, single, integral member such as a strand or filament having opposite end portions. The end portions need not be specially configured and can be essentially straight or very slightly curved and of substantially the same cross section as a central region of the stiffening element.

Although the stiffening element can have different configurations, in a preferred configuration it is formed into a portion of a loop. With this construction, the stiffening element has first and second portions or end regions and an intermediate portion between the first and second end portions. Such portions form a portion of a loop with the first and second end portions being nearer the optic than the intermediate portion. To provide an improved stiffening effect, the first and second end portions include end portions which are received in the optic.

In a preferred construction, the intraocular lens has a generally circular portion which includes the optic. The deformable element is integral with and projects from the optic and the end portions of the stiffening element are received in the optic.

The optic and deformable element are preferably constructed in one piece of the same material which may be, for example, silicone or a hydrogel. The stiffening element may be made of any one of many different materials including PMMA, polypropylene, polyamide, polyurethane, platinum, silver and a shape-memory material. When shape-memory material is used, its distorted or pre-implantion configuration may be rolled or curled and its elevated temperature condition, which would occur within the eye, would be an uncurled position suitable for fixing the optic in the eye.

The preferred way to make the intraocular lens of this invention is by insert molding, i.e. by placing the stiffening element or elements into a mold and molding or casting the optic and deformable element at the same time about the stiffening element. This results in the automatic secure attachment of both the deformable element and the stiffening element to the optic. When using this technique, it is desirable for the deformable element and the optic to be constructed of the same material.

One or more fixation members may be employed and the deformable element and the stiffening element may assume various different configurations. For example, in one construction, the deformable element completely circumscribes the optic as an annular flange. In this event, it is preferred to utilize multiple stiffening elements within the circumscribing deformable element.

Alternatively, the deformable element may include one or more deformable sections formed into at least a portion of a loop. In this event, the deformable element may include a first deformable section which is integrally joined to the optic at first and second circumferentially spaced locations. The preferred stiffening element for this configuration of deformable element is an elongated stiffening element which extends through and along the deformable section between the first and second circumferentially spaced locations.

In another embodiment, the deformable element extends from the optic and terminates in a free end. With this embodiment, both the deformable element and the stiffening element may be generally C or J-shaped.

The invention, together with additional features and advantages thereof may best be understood by reference to the following description taken in connection with the accompanying illustrative drawings.

BRIEF DESCRIPTION OF THE DRAWING

FIG. 1 is a plan view of one embodiment of an intraocular lens constructed in accordance with the teaching of the invention.

FIG. 1a is an enlarged fragmentary sectional view of a portion of FIG. 2.

FIG. 2 is a sectional view taken generally along line 2—2 of FIG. 1.

FIG. 2a is an enlarged fragmentary view partially in section showing a portion of FIG. 1.

FIG. 3 is a plan view of a second embodiment of intraocular lens constructed in accordance with this invention.

FIG. 3a is an enlarged fragmentary sectional view showing a portion of FIG. 3.

FIG. 4 is an enlarged sectional view taken generally along line 4—4 of FIG. 3.

FIG. 5 is a side elevational view of a third embodiment of the invention wherein the stiffening elements are constructed of shape memory material and are shown in the partially curled up condition prior to insertion into the eye.

FIG. 6 is a plan view similar to FIG. 1 showing a fourth embodiment of the invention.

FIG. 7 is a sectional view taken generally along line 7—7 of FIG. 6.

FIG. 8 is a plan view similar to FIG. 1 showing a fifth embodiment of the invention.

FIG. 9 is a sectional view taken generally along line 9—9 of FIG. 8.

FIG. 10 is a perspective view of one form of mold section and illustrating one of the steps in the preferred method of making the embodiment of FIGS. 1-2a.

FIG. 11 is an exploded perspective view illustrating both mold sections in an open condition and with the stiffening elements in the mold cavity after completion of a first stage of the molding process.

DESCRIPTION OF THE PREFERRED EMBODIMENT

FIGS. 1 and 2 show an IOL 11 which includes a deformable optic 13 and a fixation member 15. Fixation member 15 includes a deformable element 17 integral with the optic 13 and four resilient stiffening elements 19 received in and completely encased by the deformable element and optic 13.

The optic 13 may be of any suitable configuration, and in this embodiment is circular as viewed in plan. The optic 13 has an anterior surface 21 and a posterior surface 23. In this embodiment, the anterior surface 21 is convex and the posterior surface 23 is planar; however, these configurations are purely illustrative and no limitation is intended or implied. The deformable element 17 may have different configurations, but in the embodiment of FIGS. 1 and 2 is annular and has a circular outer periphery 25 and a circular inner periphery 27 which is contiguous the circular periphery of the optic 13. The deformable element 17 is much thinner than the optic as shown in FIGS. 1a and 2. In this embodiment, the optic 13 and the deformable element 17 are integrally molded in one piece of a silicone material.

Although it is preferred to employ a plurality of the stiffening elements 19, the four stiffening elements illustrated in FIG. 2 are purely illustrative and a greater or lesser number can be used. The stiffening elements 19 are preferably equally spaced circumferentially about optic 13.

Although the stiffening elements 19 may be differently shaped if desired, in this embodiment they are identical. The stiffening elements 19 are sufficiently stiff so that they can stiffen the deformable element 17 but also sufficiently flexible so that IOL 11 can be rolled or folded for implantation without damage to the stiffening elements or deformable element. The stiffening elements 19 are stiffer than the material from which the optic 13 and deformable element 17 are constructed. In this embodiment each of the stiffening elements 19 is preferably constructed of a single elongated strand of PMMA. Each of the stiffening elements has opposite end portions 29, and as shown in FIGS. 1a and 2a, each of the end portions is essentially straight or only slightly curved and of substantially the same circular cross section as a central region or intermediate portion 31 of the stiffening elements. Furthermore, it is not necessary to specially process or treat the end portions 29 or any other portion of the stiffening element 19 in order to attach it to the optic 13. Rather, the embedding or encasing of the stiffening element 19 within the deformable element 17 and a portion of the optic 13 serves to attach the stiffening element to the optic and to the deformable element.

Each of the deformable elements 19 is formed into a portion of a loop with the end portions 29 being received in a peripheral region 32 (FIGS. 1a and 2a) of the optic 13 and being circumferentially spaced and with the intermediate portion being located radially outwardly of the end portions 29. Although the end portions 29 are received within what has been described as the optic 13, it is not required that this peripheral region 32 be capable of functioning as a lens. Rather, the peripheral region 32, which is somewhat thickened relative to the deformable elements 17, may be considered as part of the deformable element, if desired. It is preferred, however, that the deformable element 19 extend radially inwardly into the relatively thicker peripheral region 32 so as to avoid having the relatively thicker peripheral region 32 joined to the stiffened deformable element 17 by a relatively weak section which might be subject to additional bending or kinking. Preferably the stiffening elements 19 extend radially outwardly to a location closely adjacent the outer periphery 25. By so doing, substantially the entire radial width of the relatively thin deformable element is stiffened.

With this construction, the deformable element 17 is much thinner than would be possible if the stiffening elements 19 were not utilized. The stiffening elements 19 stiffen the deformable element 17 so that when the intraocular lens 11 is implanted in a human eye, the fixation member 15 can adequately position and retain the optic 13 in the eye. They also assist in causing the deformable element to assume its desired shape when folding pressure on the IOL is released.

The deformable element 17 not only serves to retain the stiffening elements 19, but also forms a sheath around them which enables a larger variety of materials to be utilized for the stiffening elements than might otherwise be possible. Because the intraocular lens 11 is deformable, it can be rolled or folded for insertion through a small incision into the eye. Because the deformable element 19 is much thinner than the optic 13, the intraocular lens 11 is much smaller when rolled or folded than it would be if the deformable element 17 were thicker.

A preferred method of making the intraocular lens 11 is by insert molding. This results in the optic 13 and the deformable element 17 being a one-piece integral structure with the stiffening elements 19 captured in such structure.

FIGS. 3 and 3a show a variation intraocular lens 11a which is identical to the intraocular lens 11 in all respects not shown or described herein. Portions of the intraocular lens 11a corresponding to portions of the intraocular lens 11 are designated by corresponding reference numerals followed by the letter a.

The primary differences between the intraocular lenses 11 and 11a are the configurations of the deformable elements and stiffening elements. Furthermore, the intraocular lens 11a is depicted in FIG. 3 as having two identical, symmetrically-positioned fixation members 15a. Each of the fixation members 15a includes a relatively thin, U-shaped, deformable element 17a integrally joined to the thicker optic 13a at circumferentially spaced locations 33 and 35. Each of the deformable elements 17a cooperates with the optic 13a to define an opening 37.

Each of the fixation members 15a also includes a stiffening element 19a. Each of the stiffening elements 19 is in the form of an elongated, U-shaped resilient strand or filament and extends through and along the associated deformable element 17a between the associated circumferentially spaced locations 33 and 35. The end portions 29a of the stiffening elements 19a extend within the circular periphery 27a of optic 13a as best seen in FIG. 3a. Each of the stiffening elements 19a is formed into a portion of a loop which is similar in a geometric sense to the portion of the loop formed by the associated deformable element 17a.

FIG. 5 shows another variation intraocular lens 11b which is identical to the intraocular lens 11a in all respects not shown or described herein. Portions of intraocular lens 11b corresponding to portions of intraocular lens 11a are designated by corresponding reference characters with the a replaced with a b.

The intraocular lens 11b is identical to the intraocular lens 11a except that the stiffening elements 19b are constructed of shape memory material. FIG. 5 shows the stiffening elements 19b in their distorted or deformed configuration, and the original or normal (in-the-eye) configuration of the stiffening elements 19b is the same as that shown for the stiffening elements 19a in FIGS. 3 and 4.

More specifically, a shape memory member when heated to a transition temperature deforms from a distorted shape to an original shape. As indicated above, the original shape of the stiffening element 19b is the same as the configuration of the stiffening element 19a and the deformed configuration is shown in FIG. 5. In the distorted configuration of FIG. 5, the stiffening elements 19b are curled over the optic 13b, and this correspondingly curls the deformable elements 17b. The stiffening elements can be curled in any suitable manner. The stiffening elements 19b are resiliently deformable in both the original and the distorted configurations so that the entire intraocular lens 11b can be rolled or folded to a small diameter for insertion through a small incision into the eye. When placed in the eye, the temperature of the human body elevates the temperature of the stiffening elements 19b above the transition temperature so that the stiffening elements uncurl and return to their original configuration and can properly fix the intraocular lens in the eye. In returning to the original configuration, the stiffening elements 19b force the more flexible deformable elements 17b to the original configuration, which is the same as that shown in FIGS. 3 and 4 for the intraocular lens 11a.

Nitinol is one class of materials having the shape memory characteristic. Nitinol is the generic name which has been given to a family of alloys which contain both nickel and titanium. Because the stiffening elements 19b are completely encased and shielded after implantation in an eye from direct contact with the eye by the deformable elements 17b, it is anticipated that shape memory materials of this type which are not biocompatible may be safely used in the eye.

FIGS. 6 and 7 show still another variation intraocular lens 11c which is identical to the intraocular lens 11a in all respects not shown or described herein. Portions of the intraocular lens 11c corresponding to portions of the intraocular lens 11a are designated by corresponding reference numerals followed by the letter c.

The differences between the intraocular lenses 11a and 11c are the configurations of the deformable elements and stiffening elements. The intraocular lens 11c has two, symmetrically positioned, identical fixation members 15c. Each of the fixation members 15c includes a relatively thin, deformable element 17c integrally joined to the thicker optic 13c at the periphery 27c. The fixation members 15c are joined to the optic 13c at diametrically opposed locations.

Each of the deformable elements 17c extends from the optic 13c and terminates in a free end 41 which is spaced from the optic and the periphery 27c. Each of the stiffening elements 19c also terminates outwardly in a free end 43. Each of the deformable elements 17c and the stiffening elements 19c are generally J-shaped.

FIGS. 8 and 9 show another embodiment of an intraocular lens 11d which is identical to the intraocular lens 11c in all respects not shown or described herein. Portions of the intraocular lens 11d corresponding to portions of the intraocular lens 11c are designated by corresponding reference numerals followed by the letter "d."

The only difference between the intraocular lenses 11c and 11d is that the fixation members 15d are of a different configuration than the fixation members 15c. Specifically, the fixation members 15d are generally C-shaped rather than generally J-shaped. In the intraocular lens 11d, the deformable elements 17d and the resilient stiffening elements 19d are all generally C-shaped.

It is preferred to construct all of the embodiments of this invention with an insert-holding process. Although different techniques may be employed, FIGS. 10 and 11 show one preferred molding method for molding the embodiment of FIGS. 1–2a. A similar technique can be used to make all of the other illustrated embodiments of this invention.

FIG. 10 shows a lower mold section 51 having a mold cavity section 53 having a configuration to shape one side of the optic 13 and deformable element. The mold cavity section 53 has a depth sufficient to mold approximately one half of the optic 13 and the deformable element 17.

Although a single-stage molding process can be employed, in the illustrated embodiment of FIGS. 10 and 11, a two-stage molding process is used. In the first stage flowable material which is to form a portion of the optic 13 and a portion of the deformable element 17 is flowed into the mold cavity section 53 in sufficient quantity to accomplish this goal. Next, the resilient stiffening elements 19 are placed on top of the material in the mold cavity section 53 as shown in FIG. 11. This may be done after the material in the mold cavity section 53 cures, partially cures or before it begins to cure. In this latter case, the stiffening elements 19 are simply allowed to float on the surface of the flowable material in the mold cavity section 53.

Next, an upper mold section 55 having a mold cavity section 57 which is identical to the mold cavity 53 section is placed over the mold cavity section 53 with the mold cavity sections in axial alignment to form a mold cavity. In the second stage, additional flowable material is flowed through an opening (not shown) in a conventional manner into the mold cavity sections 53 and 57 to form the intraocular lens 11 of FIGS. 1–2a. The second stage of the molding process completely covers the stiffening elements 19 with the material of the deformable element 17 and the optic 13. After curing the mold sections 51 and 55 are separated, and the intraocular lens 11 is removed from the mold cavity.

Although exemplary embodiments of the invention have been shown and described, many changes, modifications and substitutions may be made by one having ordinary skill in the art without necessarily departing from the spirit and scope of this invention as defined in the appended claims.

I claim:

1. An intraocular lens comprising:
a deformable optic which can be deformed for insertion through an incision into the eye;
at least one fixation member for use in fixing the optic in the eye;
said at least one fixation member including a deformable element joined to the optic and a resilient stiffening element;
said stiffening element being an elongated strand and having opposite end portions received in circumferentially spaced regions of the optic;
said stiffening element forming a portion of a loop which opens toward the optic;
a major region of the stiffening element being received within the deformable element; and
the stiffening element stiffening the deformable element.

2. An intraocular lens as defined in claim 1 wherein substantially all of the stiffening element is received within the deformable element.

3. An intraocular lens as defined in claim 1 wherein each of said opposite end portions is essentially straight and of substantially the same cross section as a central region of the stiffening element.

4. An intraocular lens as defined in claim 1 wherein the intraocular lens has a generally circular portion which includes said optic, the deformable element is integral with and projects generally radially outwardly from the circular portion and the end portions of the stiffening element are received in the circular portion.

5. An intraocular lens as defined in claim 1 wherein the optic and the deformable element are constructed in one piece and of the same material.

6. An intraocular lens as defined in claim 1 wherein the optic and the deformable element are constructed of a material selected from the group consisting of a silicone and a hydrogel, and the stiffening element is constructed of a material selected from the group consisting of polymethylmethacrylate, polypropylene, polyamide, polyurethane, platinum, silver and a shape memory material.

7. An intraocular lens as defined in claim 1 wherein the deformable element circumscribes the optic.

8. An intraocular lens as defined in claim 7 wherein the stiffening element is a first stiffening element and the intraocular lens includes a second elongated stiffening element having opposite end portions received in circumferentially spaced regions of the optic, a major region of the second elongated stiffening element is received in the deformable element.

9. An intraocular lens as defined in claim 8 wherein the second elongated stiffening element is formed into at least a portion of a loop which opens toward the deformable element.

10. An intraocular lens as defined in claim 1 wherein the deformable element is formed into at least a portion of a loop.

11. An intraocular lens as defined in claim 10 wherein the stiffening element extend through and along the loop of the deformable portion.

12. An intraocular lens as defined in claim 1 wherein the deformable element is integrally joined to the optic at first and second circumferentially spaced locations, the stiffening element is a first stiffening element, the first stiffening element extends through and along the first deformable element between said first and second circumferentially spaced locations.

13. An intraocular lens as defined in claim 12 wherein said at least one fixation member is a first fixation member and the intraocular lens includes a second fixation member coupled to the optic generally opposite to said first fixation member.

14. An intraocular lens comprising:
a deformable optic which can be deformed for insertion through an incision into the eye;
a fixation member for use in fixing the optic in the eye;

said fixation member including an annular deformable element circumscribing the optic and joined to the optic and a plurality of resilient stiffening elements;

each of said stiffening elements being an elongated strand and having opposite end portions received in circumferentially spaced regions of the optic;

each of said stiffening elements forming a portion of a loop which opens toward the optic;

a major region of each of the stiffening elements being received within the deformable element;

said stiffening elements being circumferentially spaced;

the stiffening elements stiffening the deformable element; and the optic and the deformable element being of one piece construction and being of the same material.

* * * * *